United States Patent [19]

Bogen et al.

[11] Patent Number: 5,316,452

[45] Date of Patent: May 31, 1994

[54] DISPENSING ASSEMBLY WITH INTERCHANGEABLE CARTRIDGE PUMPS

[75] Inventors: Steven A. Bogen, Boston; Herbert H. Loeffler, Arlington, both of Mass.

[73] Assignee: Gilbert Corporation, Chicago, Ill.

[21] Appl. No.: 881,397

[22] Filed: May 11, 1992

[51] Int. Cl.⁵ .............................................. F04B 43/08
[52] U.S. Cl. ..................................... 417/412; 417/478; 604/153
[58] Field of Search ............... 417/412, 474, 478, 479; 222/181, 207, 214; 128/DIG. 12; 604/153, 151

[56] References Cited

U.S. PATENT DOCUMENTS

| | | | |
|---|---|---|---|
| 4,537,561 | 8/1985 | Xanthopoulos | 417/63 |
| 4,741,259 | 5/1988 | Ogata et al. | 99/279 |
| 4,798,580 | 1/1989 | DeMeo et al. | 604/30 |
| 4,824,337 | 4/1989 | Lindner et al. | 417/417 |
| 4,838,887 | 6/1989 | Idriss | 604/891 |
| 4,846,797 | 7/1989 | Howson et al. | 128/DIG. 12 |

Primary Examiner—Richard A. Bertsch
Assistant Examiner—Peter Korytnyk
Attorney, Agent, or Firm—Hamilton, Brook, Smith & Reynolds

[57] ABSTRACT

This invention describes a cartridge pump and dispensing assembly for applications where cartridges containing liquid reagents are interchanged often. The cartridge pump comprises a reagent reservoir which directly empties into a metering chamber. A valve is at each end of the metering chamber. The two valves are aligned in the same direction so as to allow unidirectional liquid flow. The metering chamber is made of a compressible material, such as flexible tubing, so that when an external compression is applied to the chamber, the liquid contained therein is forcibly expelled. As the compression is removed, the metering chamber resumes its former shape and draws liquid into the chamber from the reagent reservoir. A dispensing assembly with electromechanical actuators for compression of the metering chamber and a means for sensing the amount of liquid contained within the reagent reservoir are also shown.

16 Claims, 4 Drawing Sheets

DISPENSING ASSEMBLY WITH INTERCHANGEABLE CARTRIDGE PUMPS

BACKGROUND OF THE INVENTION

This invention relates to a pump mechanism for dispensing small aliquots of a fluid, such as a biological reagent. It may serve as part of an apparatus which dispenses a plurality of reagents to be dispensed in small volumes.

Current methods for dispensing reagents generally use pumps which require the priming of tubing lines leading into and out of a pump. When the pumping is finished, the tubing lines must be flushed before a different reagent can be pumped, lest cross-contamination of reagents occur. Because of the need for priming and clearing tubing lines, such types of pumps are not easily interchangeable.

Pumping systems using a syringe housing ("syringe pumps") are well known to those in the field. The syringe is first filled with a liquid. The liquid can then be accurately dispensed by applying a precise pressure on the plunger, usually by an electromechanical actuator. The distance that the plunger is depressed directly controls the amount of fluid to be dispensed. Such syringe pumps have two advantages: 1) the absence of tubing lines leading into and out of a pump which must be primed and flushed, and 2) a separation of the wetted components from the electromechanical controlling elements.

Such syringe pumps are useful in situations where repetitive dispensing of precise amounts of liquid are required. A drawback of such syringe pumps is that interchanging syringes on a single electromechanical actuator requires that the actuator mechanism be realigned with the position of the syringe plunger that is being inserted. In circumstances where the syringes need to be changed often in order to change the dispensed reagent, the need for repetitive manual intervention to align the electromechanical actuator with the position of the syringe plunger is a disadvantage. This disadvantage will be more acutely felt in a dispensing instrument with many electromechanical actuators.

SUMMARY OF THE INVENTION

A cartridge pump in accordance with the present invention may be used as a component of a movable platform containing a plurality of electromechanical actuators. In this manner, any desired liquid reagent contained in any of the cartridges can be dispensed at any location underneath the platform's reach. At the end of the working session, the cartridges can be easily replaced with different cartridges using the same electromechanical actuators without the need for aligning electromechanical actuators with the cartridges. This aspect increases the versatility of the dispensing instrument as a whole.

In accordance with the present invention, a pump cartridge comprises a reagent reservoir for containing a liquid. The reservoir has a liquid flow outlet at the bottom thereof. A metering chamber is directly connected to the liquid flow outlet of the reagent reservoir. The metering chamber comprises a compressible housing having a noncompressed shape. A one-way inlet valve and a one-way outlet valve are provided at respective ends of the compressible housing and are aligned in the same direction to allow unidirectional flow from the reservoir through the housing. The compressible housing may be compressed for the unidirectional ejection of a volume of liquid from the metering chamber. The compressible housing returns to the noncompressed shape after cessation of compression to draw an additional volume of liquid into the metering chamber.

In a dispensing assembly, a pump cartridge frame may hold the pump cartridge in a fixed position with respect to an actuator capable of compressing the compressible housing of the pump cartridge. Preferably, the actuator is an electromechanical actuator. The dispensing assembly may be mounted on a moveable platform for dispensing various reagents in various sample cells. Preferably, a plurality of electromechanical actuators are positioned adjacent to a plurality of receptacles on the frame into which a plurality of pump cartridges can be fit.

The cartridge may have one or more ridges extending outwardly from its external surface to serve as keys in grooves in a supporting frame. Cartridges may be coded by the circumferential positions of ridges to assure that cartridges containing particular reagents are inserted in appropriate locations in the frame.

The reagent reservoir may contain a plunger above the liquid in the reagent reservoir. The plunger is capable of moving within the reservoir as liquid is drawn out of the reservoir through the liquid flow outlet. Preferably, the plunger has a frictional force against the inner wall of the reservoir which is greater than the gravity pressure of the liquid in the reservoir in order to prevent spontaneous dripping of the liquid out of the outlet valve. Alternatively, the outlet valve in its normally closed position may itself have an opening pressure which is greater than the gravity pressure applied by the liquid in the reservoir. Alternatives to the plunger include a one-way valve at the top of the reservoir, a rolling diaphragm at the top of the reservoir and a small aperture at the top of the reservoir.

To reduce the flow of velocity of liquid during ejection, a nozzle with an inner diameter which is greater than the opening diameter of the outlet valve may be positioned below the outlet valve.

To absorb some of the initial force upon impact of the actuator against the tubing, the actuator may be a compressible piston hammer mounted on a piston arm.

The interchangeable pump cartridge of the present invention can be accepted into a dispensing assembly with an electromechanical actuator regardless of the amount of liquid in the cartridge reservoir. The cartridge maintains a separation of the wetted and electromechanical components and does not require priming of tubing lines before and after pumping. Moreover, it may be produced inexpensively and therefore can be disposed of when the reagent in the cartridge is exhausted. As a further advantage over syringe pumps, the cartridge pump of the present invention allows for dispersing of relatively small, precisely metered volumes.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF PREFERRED EMBODIMENT

Figure 1:
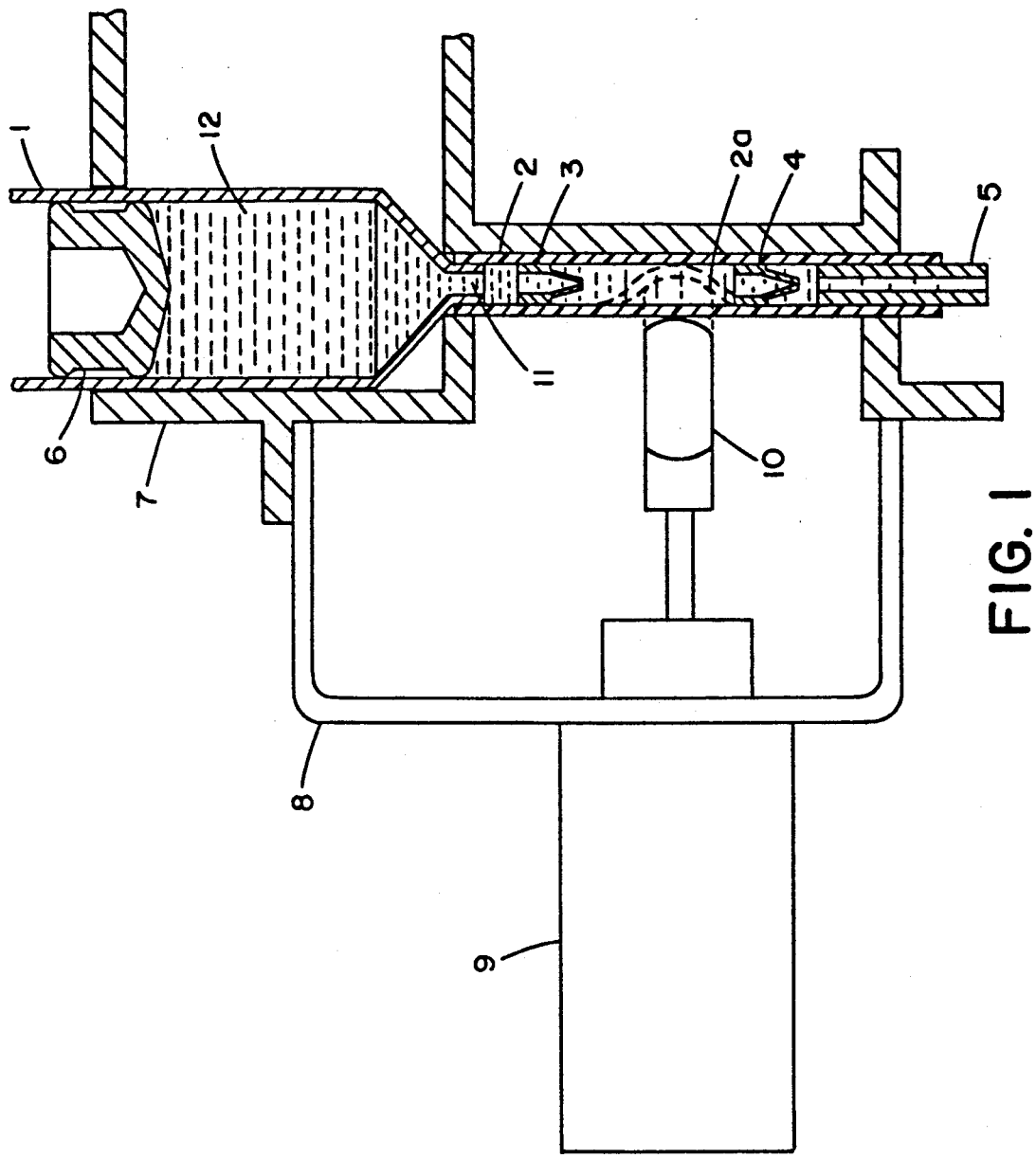
FIG. 1 is a cross-sectional view of the pump cartridge and solenoid mounted on a frame.

Referring to FIG. 1, there is a pump cartridge reservoir (1) in the shape of a cylindrical barrel. The cartridge reservoir (1) has a lower outlet (11) which is directly connected to a metering chamber comprised of a segment of compressible tubing (2), an inlet valve (3), and an outlet valve (4). The distance between the inlet valve (3) and the outlet valve (4), and the inner diameter of the tubing (2) defines a volume which can be filled with a liquid. A nozzle (5) is placed below the outlet valve (4) for the purpose of decreasing the flow velocity of the liquid. The cartridge reservoir contains a volume of liquid (12) which is sealed from above by a sliding plunger (6). The cartridge reservoir (1), plunger (6), metering chamber, and nozzle (5) are the components of the cartridge pump. The cartridge pump rests on a frame (7) which can be made of plastic. A single frame (7) can hold a plurality of pump cartridges. The frame (7) can be removed from the chassis (8) by simply lifting the frame, thereby lifting all the cartridge pumps with it. In this manner, the wetted components can be easily separated from the electromechanical components.

When an electrical current is applied to the solenoid (9), the arm extends forcefully, thereby pressing the rubber hammer (10) against the outer wall of the metering chamber tubing (2). This action deforms the tubing, causing the compressible tubing to assume a compressed shape 2a. Since the total volume inside the metering chamber between the valves (3) and (4) is decreased, a volume of liquid is expelled in the direction defined by the valves (3) and (4). In FIG. 1, the valves are shown as allowing fluid in the downward direction only. Since the diameter of the outlet valve (4) leaflets is comparatively narrow relative to the diameter of the tubing (2), the fluid has a high flow velocity. This results in a forceful squirting of the liquid. This aspect is often undesirable, since it may lead to splattering of the liquid if the object surface of the fluid is situated immediately below. Therefore, a nozzle (5) is placed below the outlet valve (4). The nozzle has an inner diameter greater than the diameter of the outlet valve (4) leaflets. This aspect causes the high velocity fluid to first accumulate in the space above and within the inner aspect of the nozzle. The liquid thus exits the nozzle (5) at a slower velocity, ideally in a dropwise manner.

The rubber hammer (10) is also compressible in order to further decrease the flow velocity of the liquid. Most solenoids tend to extend suddenly and forcefully. This results in a very rapid compression of the tubing (2). In order to decrease this rate of compression, the solenoid arm is fitted with a compressible rubber hammer (10) which absorbs some of the initial force upon impact with the tubing (2).

The tubing (2) can be made of silicone rubber, vinyl, polyurethane, flexible polyvinyl chloride (PVC) or other synthetic or natural elastomers. Such types of tubing are commonly used for peristaltic pumps. The valves can be obtained from Vernay Laboratories, Inc., Yellow Springs, Ohio, 45387 (part #VL 743-102).

When the electrical current is removed from the solenoid (9), the arm and rubber hammer (10) is retracted from the surface of the tubing (2). The tubing in the compressed position (2a) thereby reverts back to its native position (2) because of the resiliency of the tubing. The reversion of the tubing to its native position results in a negative pressure being created within the metering chamber, causing liquid (12) to be drawn from the pump reservoir (1) into the metering chamber. The metering chamber is therefore automatically primed for the next pump cycle.

Figure 2:
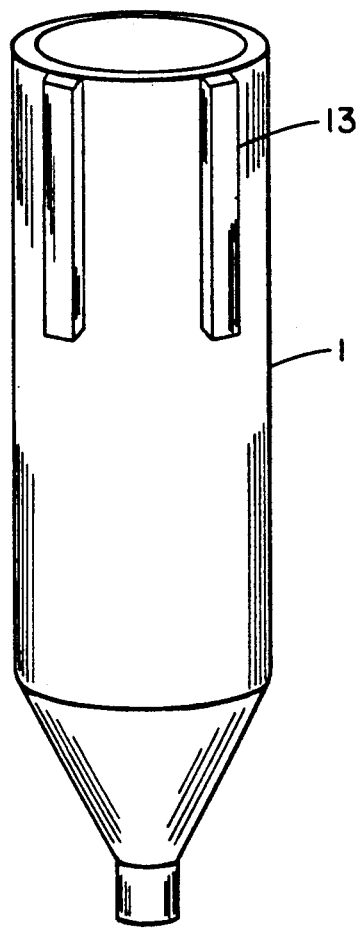
FIG. 2 is a perspective view of the pump cartridge reservoir.

Referring to FIG. 2, the outer aspect of the pump cartridge reservoir (1) has longitudinal ridges (13). These ridges fit into grooves in the frame (FIG. 1, #7) in a lock and key fashion. Different cartridges are manufactured with different patterns of ridges in order to identify the contents. In this manner, any particular cartridge will fit only into a position of the frame with a corresponding pattern of grooves. This feature will prevent the possibility of the operator placing the cartridge in an unintended position of the frame.

Figure 3:
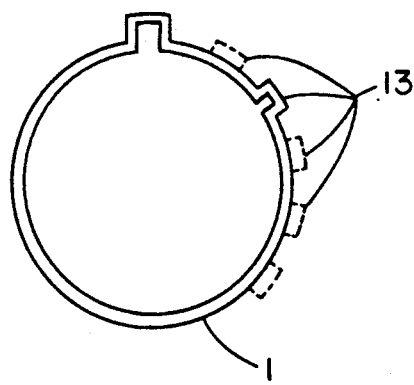
FIG. 3 is a view from above of the pump cartridge.

Referring to FIG. 3, this shows the variety of possible positions for ridges (13) on the outer surface of the pump cartridge reservoir (1).

Figure 4:
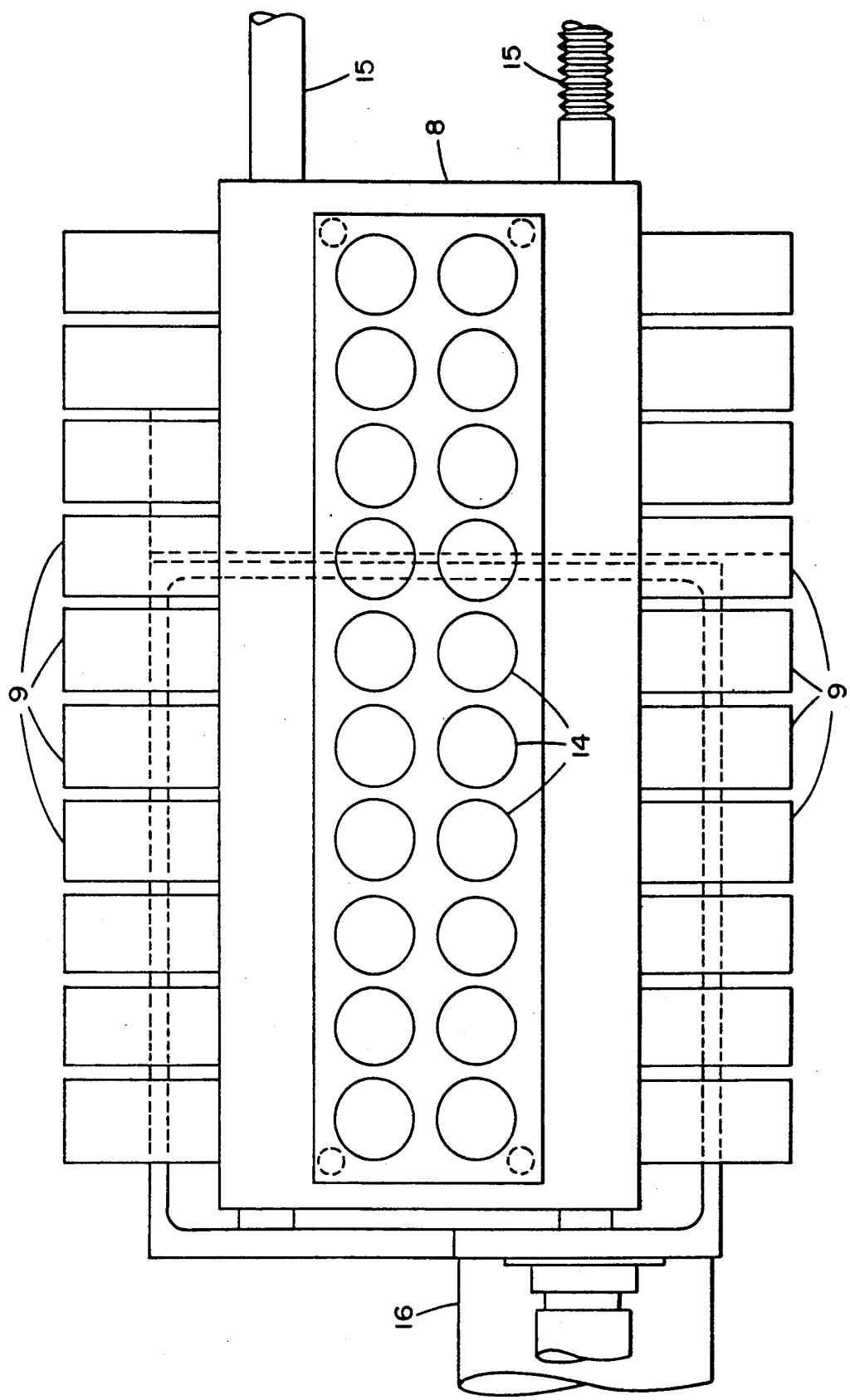
FIG. 4 is a view from above of a plurality of pump cartridges mounted on a frame and chassis of an X-Y axis robot.

Referring to FIG. 4, this shows the reagent dispensing assembly comprising a plurality of pump cartridges (14) in position on the chassis (8) with solenoid (9) for each pump cartridge. The chassis is mounted on a pair of cylindrical bars (15). In this case one of the bars is threaded and attached to a motor (16). Alternatively, a cable drive may be provided. The motor can be a conventional stepping motor or servo motor and driven by a computer-generated signal through an electronic interface.

An important aspect of the above-described invention is its ability to retain the fluid until such time as the solenoid hammer (10) presses on the metering chamber tubing (2). As will be noted from FIG. 1, both one-way valves (3 and 4) are aligned in the same direction, allowing only downward flow. It was found during construction that using valves with a low opening ("cracking") pressure resulted in the liquid dripping out of the nozzle. There are two solutions to this problem. The most obvious is to use valves with an opening pressure greater than the pressure head of liquid. In this manner, the outlet valve will not allow fluid exit until a certain minimum force is applied which is greater than the pressure head of the standing liquid.

A second alternative to prevent spontaneous dripping of the liquid out of the outlet valve (4) is to use a plunger (6) with an amount of friction against the inner surface of the reservoir (1) greater than the gravity pressure of the liquid (12). An additional advantage of the plunger (6) is that it prevents spillage of the liquid (12) from the top of the reservoir (1) (which would likely occur if the reservoir were left open from above). In this manner, the plunger will not be drawn downwards inside the reservoir merely by the weight of the liquid. However, when the metering chamber is emptied and a small amount of liquid is drawn from the reservoir (1) to refill the metering chamber, the plunger's friction to the reservoir wall is overcome. The plunger (6) thereby moves downward a distance proportional to the volume of liquid expelled. We have found it useful to apply a thin coat of a lubricant such as petroleum jelly to ensure that the plunger (6) moves smoothly downward within the reservoir (1).

Any combination of valve opening pressure and plunger friction may be used to prevent dripping, but given the low opening pressure typically found in valves of the type used, friction greater than gravity pressure of the liquid is preferred.

Figure 5:
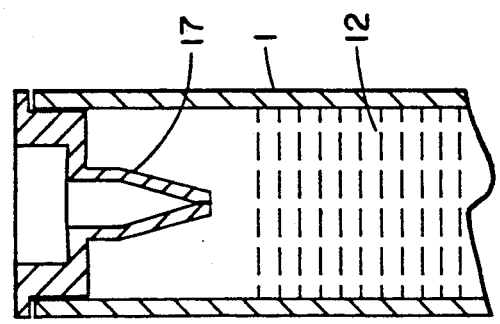

FIG. 5 shows another alternative construction of the cartridge top. Instead of using a plunger, a one-way valve (17) is placed at the top of the reservoir (1). The valve (17) has an opening pressure greater than the gravity pressure of the liquid within the reservoir. This third valve (17) is aligned in the same direction as the metering chamber valves (3 and 4). This allows the entrance of air into the reservoir as liquid is removed. In this case, cracking pressure of any or all of the three valves 3, 4 and 17 prevents spontaneous dripping from the outlet valve. Additionally, ithe valve (17) prevents spillage of the contents of the reservoir.

Figure 6:
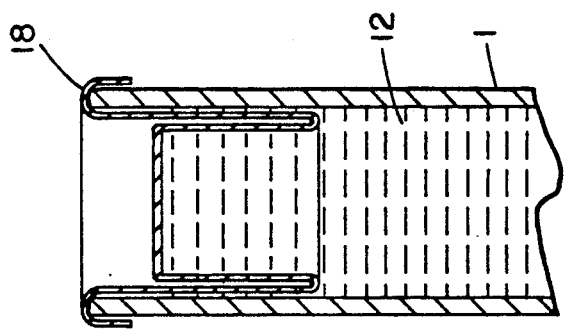

FIG. 6 shows another alternative construction for the top of the cartridge. A rolling diaphragm cover (18) is mounted at the top of the reservoir (1) and is drawn into the reservoir as the liquid is used up. This construction prevents spillage of the liquid (12) as well as provides a seal to prevent air entry. The rolling diaphragm can be made of any thin flexible elastomer such as natural rubber. The top of the rolling diaphragm can be sealed to the reservoir wall (1) by stretching the diaphragm over the reservoir, with an adhesive or by heat sealing.

Figure 7:
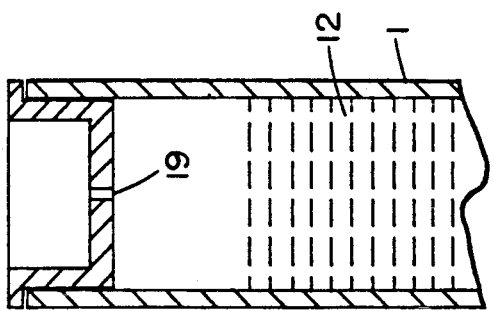
FIGS. 5–7 are cross-sectional views of the uppermost portion of the cartridge reservoir, demonstrating alternative constructions.

FIG. 7 demonstrates a third alternative construction. The top of the reservoir is closed, except for a small aperture (19) for the entrance of air. The diameter of the aperture at the top of the reservoir can be sufficiently small to effectively prevent accidental spillage of the liquid contents of the cartridge but still allow air entry as liquid is dispensed from the cartridge.

A fluid level sensor may be provided adjacent to the cartridge reservoir. For example, a shaft can be connected to the top of the plunger. The shaft can be designed with a shape such that as it is drawn into the cartridge reservoir, it can optically or electrically open or close a circuit at a certain depth within the cartridge reservoir. In this manner, the shaft connected to the plunger can signal to a computer the depth of entry into the cartridge reservoir. The depth of entry would therefore be directly proportional to the amount of liquid remaining in the cartridge reservoir. Such an arrangement provides an automatic means for sensing the amount of liquid remaining inside the reservoir.

A variety of different electromechanical actuators may be used to apply pressure on the metering chamber tubing. Although a push-type of electrical solenoid is shown in FIG. 1, a rotary or pull-type could also be used with slight modifications to the design, as would be obvious so as to apply a pressure on the metering chamber tubing. Additionally, a solenoid valve could also be used to control pressure to a pneumatic cylinder whose piston rod is the actuator. Alternatively, a piezoelectric transducer may apply the pressure to the metering chamber tubing.

While this invention has been particularly shown and described with references to preferred embodiments thereof, it will be understood by those skilled in the art that various changes in form and details may be made therein without departing from the spirit and scope of the invention as defined by the appended claims. For example, the pump is operable with the metering chamber positioned above the reservoir. Disclosure Document No. 252981 filed May 10, 1990 at the U.S. Patent and Trademark Office shows details of a potential system embodying the present invention.

We claim:

1. A dispensing assembly comprising:
   A) a plurality of pump cartridges, each pump cartridge comprising:
      i) a reservoir for containing a liquid, said reservoir having a liquid flow outlet,
      ii) a metering chamber extending below the reservoir, said metering chamber directly connected to said liquid flow outlet, said metering chamber comprising a compressible housing having an noncompressed shape, and
      iii) a one-way inlet valve and a one-way outlet valve at each end of said compressible housing, said valves aligned in the same direction so as to allow unidirectional fluid flow from the reservoir;
   B) an electrically driven reciprocating hammer actuator capable of compressing said compressible housing of each pump cartridge to eject a volume of liquid from the metering chamber thorough the outlet valve, and then release the housing to return the housing to the non-compressed shape to draw a volume of liquid with the metering chamber through the inlet valve;
   C) a pump cartridge frame with a plurality of receptacles into which said plurality of pump cartridges are fit for holding each pump cartridge in a fixed position with respect to said actuator; and
   D) a second frame supporting the actuator and removably receiving the pump cartridge frame with the plurality of receptacles as a unit to position each pump cartridge adjacent to the actuator, the first frame being removable from the second frame by lifting the first frame to lift all of the plurality of pump cartridges away from the second frame and the actuator.

2. A dispensing assembly according to claim 1 wherein said reservoir contains a plunger above said liquid in said reagent reservoir, said plunger being capable of moving within said reservoir as liquid is drawn out of said reservoir through said liquid flow outlet.

3. A dispensing assembly according to claim 2 wherein said plunger has a frictional force against the inner wall of said reservoir greater than said gravity pressure of said liquid in said reservoir.

4. A dispensing assembly according to claim 1 wherein said reservoir has a one-way valve at the top of said reservoir.

5. A dispensing assembly according to claim 1 wherein said reservoir has a rolling diaphragm at the top of said reservoir.

6. A dispensing assembly according to claim 1 wherein said reservoir has a small aperture at the top of said reservoir.

7. A dispensing assembly according to claim 1 wherein each pump cartridge has on its external surface one or more ridges projecting outward from the external surface of said cartridge serving as keys.

8. A dispensing assembly according to claim 1 with a means for reducing the flow velocity of said liquid during said ejection comprising a nozzle with an inner diameter which is greater than the opening of said outlet valve.

9. A dispensing assembly according to claim 1 wherein said outlet valve is normally closed and has an opening pressure greater than the gravity pressure applied by said liquid in said reservoir.

10. A dispensing assembly according to claim 1, wherein said cartridge has on its external surface one or more ridges projecting outward from the external surface of said cartridge serving as keys and said frame has a means for accommodating said ridges of said pump cartridge.

11. A dispensing assembly according to claim 1 which further includes:
a plurality of electromechanical actuators.

12. A dispensing assembly according to claim 1 which further includes a compressible piston hammer mounted on a piston arm of said actuator.

13. A dispensing assembly according to claim 1 wherein the reservoir contains biological reagent.

14. A dispensing assembly as claimed in claim 1 wherein the second frame is a moveable platform.

15. A pump cartridge assembly for dispensing liquid from a plurality of pump cartridges comprising:
A) a pump cartridge frame with a plurality of receptacles into which a plurality of pump cartridges are fit, each pump cartridge comprising:
  i) a reagent reservoir for containing liquid, said reservoir having a liquid flow outlet,
  ii) a metering chamber extending below the reservoir, said metering chamber being directly connected to said liquid flow outlet, said metering chamber comprising a compressible housing having a non-compressed shape, and
  iii) a one-way inlet valve and a one-way outlet valve at each end of said compressible housing, said valves aligned in the same direction so as to allow unidirectional fluid flow from the reservoir; and
B) the pump cartridge frame and the plurality of pump cartridges being removable as a unit from an actuator assembly, the actuator assembly having an electrically driven reciprocating hammer for compressing each compressible housing for the unidirectional ejection of a volume of liquid from said metering chamber and the pump cartridge, said compressible housing returning to said noncompressible shape after cessation of compression by the hammer to draw an additional volume of liquid into said metering chamber, the pump cartridge frame being removable from the actuator assembly by lifting the pump cartridge frame to lift all of the plurality of pump cartridges away from the actuator assembly, removal of the pump cartridges removing all dispensing surfaces wetted by fluid from said reagent reservoir.

16. A method of dispensing liquid comprising:
A) providing an actuator assembly which includes an electrically driven reciprocating hammer;
B) positioning as a unit a plurality of pump cartridges, on a pump cartridge frame, within the actuator assembly, each pump cartridge comprising:
  i) a reagent reservoir for containing a liquid, said reservoir having a liquid flow outlet,
  ii) a metering chamber extending below the reservoir, said metering chamber being directly connected to said liquid flow outlet, said metering chamber comprising a compressible housing having an non-compressed shape, and
  iii) a one-way inlet valve and a one-way outlet valve at each end of said compressible housing, said valves aligned in the same direction so as to allow unidirectional fluid flow from the reservoir;
C) compressing the compressible housing with the reciprocating hammer of the actuator assembly to unidirectionally eject a volume of liquid from said metering chamber and the pump cartridge;
D) returning the reciprocating hammer to return the compressible housing to its noncompressed shape to draw an additional volume of liquid into said metering chamber; and
E) removing the pump cartridge frame and pump cartridges as a unit from the actuator assembly by lifting the pump cartridge frame to lift all of the plurality of pump cartridges away form the actuator assembly, removal of the pump cartridges providing for replacement of all dispensing surfaces wetting by fluid from said regent reservoirs.

* * * * *

UNITED STATES PATENT AND TRADEMARK OFFICE
CERTIFICATE OF CORRECTION

PATENT NO.   : 5,316,452
DATED        : May 31, 1994
INVENTOR(S)  : Steven A. Bogen and Herbert H. Loeffler It is certified that error appears in the above-identified patent and that said Letters Patent is hereby corrected as shown below:

Column 1,
Line 4, insert the following:

-- GOVERNMENT SUPPORT
 This invention was made with government support under Grant Number 2R44AI 29778-02 awarded by the National Institutes of Health. The government has certain rights in the invention. --

Signed and Sealed this

Twenty-third Day of October, 2001

Attest:

NICHOLAS P. GODICI
Attesting Officer   Acting Director of the United States Patent and Trademark Office